United States Patent [19]

Henley

[11] Patent Number: 5,069,908

[45] Date of Patent: Dec. 3, 1991

[54] CROSSLINKED HYDROGEL AND METHOD FOR MAKING SAME

[75] Inventor: Ernest J. Henley, Houston, Tex.

[73] Assignee: Henley International, Inc., Sugar Land, Tex.

[21] Appl. No.: 533,805

[22] Filed: Jun. 6, 1990

Related U.S. Application Data

[63] Continuation-in-part of Ser. No. 367,783, Jun. 19, 1989, abandoned.

[51] Int. Cl.$^5$ ............................................. A61F 13/00
[52] U.S. Cl. ................................... 421/449; 442/482; 442/485
[58] Field of Search ............... 424/443, 448, 449, 484, 424/485, 486

[56] References Cited

U.S. PATENT DOCUMENTS 4,349,470 9/1982 Battista .................................. 527/202
4,853,227 8/1989 Kurihara-Bergstrom .......... 424/443

Primary Examiner—Thurman K. Page
Assistant Examiner—Leon R. Horne
Attorney, Agent, or Firm—Jennings, Carter, Thompson & Veal

[57] ABSTRACT

A chemically crosslinked hydrogel includes an active ingredient for transdermal transport selected from the group of lidocainehydrochloride, hydrocortisone, menthol, and methyl salicylate and utilizes as a crosslinking agent an aluminum acetate, which is a polyvalent salt, which renders the resulting hydrogel electrically conductive with a resistance of less than 10,000 ohms per linear centimeter.

10 Claims, 1 Drawing Sheet

CROSSLINKED HYDROGEL AND METHOD FOR MAKING SAME

This is a continuation-in-part of application Ser. No. 367,783 filed on June 19, 1989, now abandoned.

FIELD OF THE INVENTION

The present invention relates to the field of conductive gels used for transdermal drug application and more particularly to chemically crosslinked hydrogels which retain an active ingredient in prolonged contact with the skin for enhanced drug applications such as are associated with TENS treatment, iontophoresis, and phonophoresis.

BACKGROUND OF THE INVENTION

Topical application of medication in the form of dermally applied cremes is commonplace. Numerous non-prescription products containing methyl salicylate, hydrocortisone, lidocainehydrochloride, or benzocaine may be purchased off the shelf at any drug store. In these cremes, the active ingredient is mixed with water and assorted high molecular weight waxes and emulsifiers, such as propylene glycol, lanolin, stearic acid, and ethyl alcohol, to form a creme which can be rubbed into the skin. Also known are iontophoresis, the introduction of various ions through the skin by electricity, and phonophoresis which is the transdermal introduction of substance into the body by means of ultrasound. However, iontophoresis has always used sponges or the like soaked in medicated water to provide the source of the transfer medicants whereas phonophoresis has used cremes.

Hydrogels are also well known and have been used in conjunction with medical electrodes. U.S. Pat. No. 4,706,680 issued Nov. 17, 1987 lists numerous patents which disclose hydrophilic gels and medical electrodes employing them. However, none of these patents appear to be directed to a chemically crosslinked hydrogel wherein the crosslinking agent also is the electrical conductivity agent.

SUMMARY OF THE INVENTION

The object of the present invention is to provide a chemically crosslinked hydrogel which would act as a carrier for a medicant to be applied transdermally over a long period of time.

Another object of the invention is to provide a chemically crosslinked hydrogel which contains an active ingredient susceptible to transfer in iontophoresis and phonophoresis.

A further object of the invention is to provide a medicated electrode for TENS application using biphasic waveforms.

For both iontophoresis and TENS application, the gels must be highly conductive. Traditionally monovalent salts such as sodium chloride or magnesium acetate have been added to the media so that electrical resistance is lowered below 10,000 ohms per linear centimeter. In the present invention, I have determined aluminum acetate, which is a polyvalent salt, can be used to both crosslink a hydrogel and to render the gel sufficiently conductive to be suitable for TENS or iontophoresis applications. It is desirable to use crosslinked hydrogels as the media because crosslinked hydrogels do not melt, thus the gel containing the active ingredient can be affixed to the skin of a patient using an adhesive tape and left on for an extended period of time. Over a period of time, the water in the gel will slowly evaporate. For example, a one-sixteenth inch thick hydrogel would dry in about 24 hours. The active ingredient or medicant is absorbed into the body by transdermal transport. Of course, a much more rapid absorption would be expected if the medicated hydrogel were used with an iontophoresis electrode or was the media for phonophoresis. Of course, the biphasic waveforms of the TENS application do not lend themselves to iontophoresis, thus although TENS may not increase the absorption rate, it will be appreciated that the TENS electrode may be worn over an extended period of time during which the therapy is intermittently applied. Thus, by medicating the electrodes in a manner that facilitates wearing of the electrode and transdermal transport, the patient receives continuous therapeutic and analgesic benefits.

The therapeutic and analgesic benefits of the selected medicants are well known, the medicants or active ingredients being lidocainehydrochloride, menthol hydrocortisone, and methyl salicylate, each of which are commonly used for such purposes. Because of various incompatibilities, there are some differences in the formulation of each hydrogel, however each contains the aluminum acetate as the crosslinking agent.

BRIEF DESCRIPTION OF THE DRAWINGS

Apparatus embodying features of my invention are depicted in the attached figures which form a portion of this invention and wherein.

DESCRIPTION OF THE PREFERRED EMBODIMENT

Figure 1:
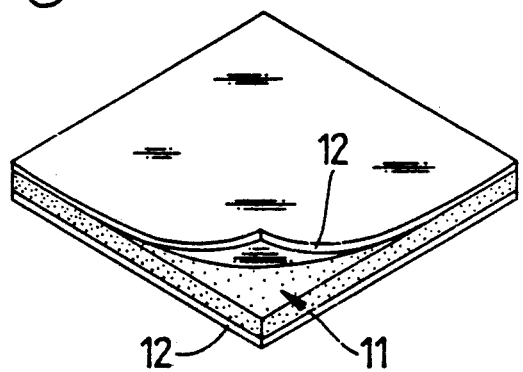
FIG. 1 is a perspective view of my crosslinked hydrogel with a peelable release paper on each side.
Figure 2:
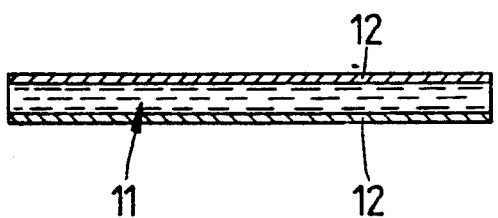
FIG. 2 is a sectional view of the embodiment of FIG. 1.

Referring to the Figures for a better understanding of the invention, it will be appreciated that a chemically crosslinked hydrogel will remain solid and in gel form as long as the water content is retained, therefore it is desirable to enclose the hydrogel 11 within a removable container such as a peelable release paper 12 as shown in FIGS. 1 and 2. It will be appreciated that the hydrogel 11 can be formed and packaged in this manner by conventional methods such as passing the plastic hydrogel 11 through a set of forming rollers with strips of release paper 12 on either side. Likewise the gel can be cured in molds of various shapes and sizes and individually packaged. The crosslinked hydrogels 11 thus formed and in accordance with my invention include a medicant as an active ingredient which when placed into contact with the skin of a patient will be received into the patient's system via transdermal transport. The preferred active ingredients are lidocainehydrochloride, hydrocortisone, menthol, and methyl salicylate, although other well-known ingredients used in topical applications may be useful.

Figure 3:
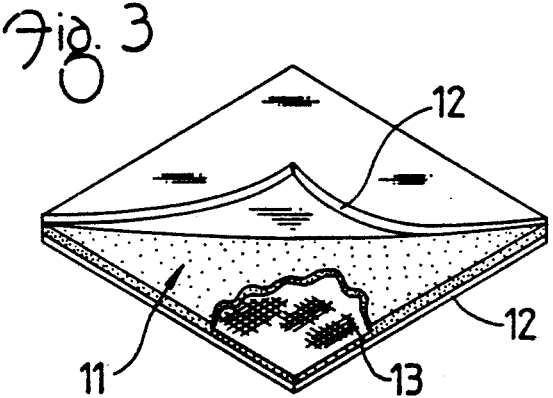
FIG. 3 is a perspective view partially in section of my crosslinked hydrogel with an internal scrim and peelable release paper on either side.
Figure 4:
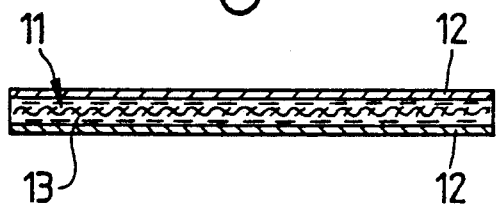
FIG. 4 is a sectional view of the embodiment of FIG. 3.

In FIGS. 3 and 4, the hydrogel is formed with a scrim 13 contained internally, the scrim 13 may be gauze or a paper towel and serves to strengthen the hydrogel.

In each of my hydrogels, I have utilized aluminum acetate as the crosslinking and ionization agent, however each active ingredient requires a somewhat different formulation as shown in the tables below. It should be understood that is is difficult to achieve the desired stabilization of the hydrogels in that if they are excessively crosslinked, the product tends to decompose, while under-crosslinking leaves the product too fluid.

TABLE I

| Lidocainehydrochloride Formulation #1 | |
|---|---|
| 100 cc | Water |
| 1.4 g | Carboxymethylcellulose |
| 2.0 g | Lidocainehydrochloride |
| 7.2 g | Gelatin |
| 3.0 g | Polyethylene glycol |
| 0.17 g | Aluminum acetate |

TABLE II

| Lidocainehydrochloride Formulation #2 | |
|---|---|
| 100 cc | Water |
| 1.4 g | Carboxymethylcellulose |
| 2.0 g | Lidocainehydrochloride |
| 3.0 g | Polyethylene glycol |
| 0.7 g | Menthol |
| 0.17 g | Aluminum acetate |

TABLE III

| Limits on Lidocainehydrochloride Formulation/ 100 cc Water | |
|---|---|
| 1.2 to 1.7 g | Carboxymethylcellulose |
| up to 4.0 g | Lidocainehydrochloride |
| 0.0 to 8.0 g | Gelatin |
| 0.0 to 6.0 g | Polyethylene glycol |
| 0.0 to 2.0 g | Menthol |
| 0.17 to 0.50 g | Aluminum acetate |

TABLE IV

| Hydrocortisone Formulation | |
|---|---|
| 100 cc | Water |
| 1.4 g | Carboxymethylcellulose |
| 0.5 g | Hydrocortisone |
| 3.2 g | Polyethylene glycol |
| 1.0 g | Menthol |
| 0.16 g | Lanolin |
| 0.17 g | Aluminum acetate |

TABLE V

| Limits on Hydrocortisone Formulation/ 100 cc Water | |
|---|---|
| 1.1 to 1.6 g | Carboxymethylcellulose |
| up to 0.5 g | Hydrocortisone |
| 2.0 to 5.0 g | Polyethylene glycol |
| 0.0 to 5.0 g | Menthol |
| 0.0 to 1.0 g | Lanolin |
| 0.17 to 0.50 g | Aluminum acetate |

TABLE VI

| Methyl Salicylate Formulation | |
|---|---|
| 100 g | Water |
| 1.4 g | Carboxymethycellulose |
| 6.67 g | Methyl salicylate |
| 1.32 g | Menthol |
| 2.7 g | Polyethylene glycol |
| 0.14 g | Lanolin |

TABLE VI-continued

| Methyl Salicylate Formulation | |
|---|---|
| 0.2 g | Aluminum acetate |

TABLE VII

| Limits on Methyl Salicylate Formulation/ 100 cc Water | |
|---|---|
| 1.2 to 1.6 g | Carboxymethylcellulose |
| 3.0 to 8.0 g | Methyl salicylate |
| 0.5 to 5.0 g | Menthol |
| 2.0 to 3.5 g | Polyethylene glycol |
| 0.0 to 2.2 g | Lanolin |
| 0.20 to 0.50 g | Aluminum acetate |

As may be seen from the tables, the chemicals used in each formulation are readily commercially available from a variety of sources.

Figure 5:
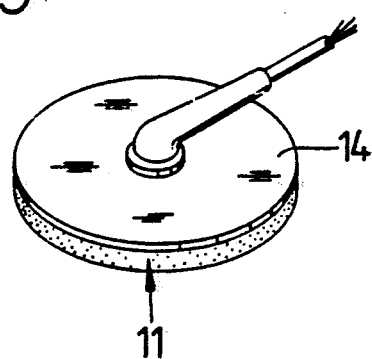
FIG. 5 is a perspective view of my hydrogel in conjunction with a treatment device.
Figure 6:
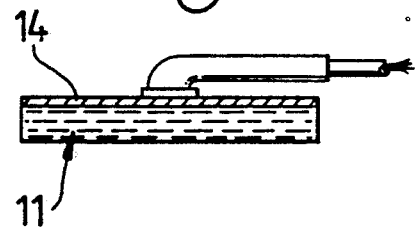
FIG. 6 is a sectional view of the embodiment of FIG. 5.

To produce any one of the formulations all of the ingredients listed in the specific tables, e.g. Table IV, except the crosslinking agent, aluminum acetate, are mixed at once and heated at about 160 degrees Fahrenheit for one hour. The solution is then cooled to below 120 degrees, whereupon the required amount of aluminum acetate is added. The solution may then be fabricated into any of the products shown in FIGS. 1-6. For example, solid discs, rectangles or squares may be made by pouring the solution into appropriately shaped molds to the desired thickness. Electrodes, such as shown in FIGS. 5 and 6, may be made by spraying or painting the solution on a conductive carbon or silicon electrode 14 which can provide electrical connection for TENS or iontophoresis treatment. Or the hydrogel may be painted or sprayed onto a scrim 13, or fed through rollers together with the release paper and scrim, which permits the fabrication of thinner hydrogels due to the structural support of the scrim. The curing time for crosslinking of the hydrogel is from about four to about twenty-four hours at room temperature.

While I have shown my invention in various forms, it will be obvious to those skilled in the art that it is not so limited but is susceptible of various changes and modifications without departing from the spirit thereof.

What I claim is:

1. A crosslinked hydrogel for use in transcutaneous electrical nerve stimulation and iontophoresis to provide transdermal delivery of an active ingredient comprising:
   (a) an active ingredient selected from the class of lidocainehydrochloride, hydrocortisone, menthol or methyl salicylate;
   (b) a crosslinking agent, aluminum acetate in a quantity of about 0.1% to about 0.5% by weight to provide ionic conductivity in said hydrogel;
   (c) water;
   (d) an emulsifier selected from the class of propyleneglycol, lanolin, stearic acid or ethyl alcohol; and
   (e) carboxymethylcellulose in an amount of between 1.1% to 1.7% by weight, wherein said hydrogel is characterized by having an electrical resistance of less than 10,000 ohms per linear centimeter.

2. A crosslinked hydrogel as defined in claim 1 wherein said hydrogel contains less than about 4% by weight lidocainehydrochloride as an active ingredient.

3. A crosslinked hydrogel as defined in claim 1 containing up to 0.5% hydrocortisone by weight as the active ingredient.

4. A crosslinked hydrogel as defined in claim 3 containing from about 0.0% to about 2.0% menthol.

5. A crosslinked hydrogel as defined in claim 1 further comprising a scrim supporting said gel in a predetermined shape.

6. A crosslinked hydrogen containing an active ingredient for transdermal medical application comprising:
(a) water;
(b) an active ingredient selected from the class of menthol, methyl salicylate, lidocainehydrochloride or hydrocortisone;
(c) aluminum acetate, a crosslinking agent providing ionic conductivity to said hydrogel, in a quantity of about 0.1% to about 0.5% by weight such that hydrogel has a resistance of less than 10,000 ohms per linear centimeter; and
(d) carboxymethylcellulose in an amount of between about 1.1% to 1.7% by weight.

7. A crosslinked hydrogel as defined in claim 6 containing from about 3% to about 8% by weight methyl salicylate.

8. A crosslinked hydrogel as defined in claim 6 containing up to about 1.0% by weight hydrocortisone.

9. A crosslinked hydrogel as defined in claim 6 containing up to about 4% lidocainehydrochloride.

10. A crosslinked hydrogel as defined in claim 6 containing between 1.4 g and 1.7 g of carboxymethylcellulose.

* * * * *